(12) United States Patent
Kim et al.

(10) Patent No.: US 12,171,996 B2
(45) Date of Patent: Dec. 24, 2024

(54) CUSTOMIZED ELECTRICAL STIMULATION PROVIDING SYSTEM AND METHOD THEREOF

(71) Applicant: Daegu Gyeongbuk Institute of Science and Technology, Daegu (KR)

(72) Inventors: Min Seok Kim, Daegu (KR); Min Young Kim, Daegu (KR); Hyun Young Shin, Suwon-si (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 665 days.

(21) Appl. No.: 17/390,156

(22) Filed: Jul. 30, 2021

(65) Prior Publication Data
US 2022/0032040 A1 Feb. 3, 2022

(30) Foreign Application Priority Data
Jul. 30, 2020 (KR) .................. 10-2020-0094870

(51) Int. Cl.
*A61N 1/04* (2006.01)
*A61N 1/36* (2006.01)

(52) U.S. Cl.
CPC ....... *A61N 1/0452* (2013.01); *A61N 1/36031* (2017.08)

(58) Field of Classification Search
CPC .............. A61N 1/0452; A61N 1/36031; A61N 1/3603; A61N 1/36034; A61N 1/36003; A61N 1/328
See application file for complete search history.

(56) References Cited

U.S. PATENT DOCUMENTS

2015/0196767 A1* 7/2015 Ahmed .............. A61N 1/36062
607/117
2015/0224309 A1* 8/2015 Ajiki ................... A61N 1/0452
607/48

FOREIGN PATENT DOCUMENTS

| KR | 10-2014-0088407 A | 7/2014 |
| KR | 10-1692920 B1 | 1/2017 |
| KR | 10-2018-0057194 A | 5/2018 |
| KR | 10-2019-0014887 A | 2/2019 |
| KR | 10-1977734 B1 | 5/2019 |

(Continued)

OTHER PUBLICATIONS

Korean Office Action dated Aug. 17, 2023 for corresponding Korean Patent Application No. 10-2023-0087744, 8 pages.

(Continued)

*Primary Examiner* — Amanda K Hulbert
*Assistant Examiner* — Philip C Edwards
(74) *Attorney, Agent, or Firm* — Hauptman Ham, LLP

(57) ABSTRACT

A customized electrical stimulation providing system includes: an electrical stimulation request input unit receiving electrical stimulation mode selection information; an electrical stimulation control unit setting an electrical stimulation control variable according to the electrical stimulation mode selection information and generating a control signal; and an electrical stimulation providing means receiving the control signal generated by the electrical stimulation control unit and providing electrical stimulation, wherein the electrical stimulation mode selection information includes at least one of a beauty mode (muscle loss mode) and a muscle strengthening mode.

12 Claims, 11 Drawing Sheets

(56) References Cited

FOREIGN PATENT DOCUMENTS

KR     10-2020-0005899 A     1/2020
KR        10-2098056 B1     4/2020

OTHER PUBLICATIONS

Nishida et al., "Review of the evidence on the use of electrical muscle stimulation to treat sarcopenia," European Geriatric Medicine, 2016, pp. 267-271, vol. 7, 5 pages.
Korean Office Action issued on Jul. 18, 2022, in connection with the Korean Patent Application No. 10-2020-0094870.
Korean Notice of Allowance dated Apr. 13, 2023 for corresponding Korean Patent Application No. 10-2020-0094870, 4 pages.
Korean Office Action issued on Jan. 19, 2022, in connection with the Korean Patent Application No. 10-2020-0094870 .

* cited by examiner

CUSTOMIZED ELECTRICAL STIMULATION PROVIDING SYSTEM AND METHOD THEREOF

CROSS-REFERENCE TO RELATED APPLICATIONS

This application claims priority under 35 U.S.C. § 119 to Korean Patent Application No. 10-2020-0094870, filed on Jul. 30, 2020, in the Korean Intellectual Property Office, the disclosure of which is incorporated herein by reference in its entirety.

TECHNICAL FIELD

The following disclosure relates to a customized electrical stimulation providing system and method, and more particularly, to a customized electrical stimulation providing system and method capable of providing customized electrical stimulation according to a senescence degree of somatic cells (muscle cells or the like).

BACKGROUND

As many countries such as Japan and Europe as well as Korea have entered a super-aged society, productive population in the many countries has decreased.

A reduction in muscle (muscle reduction) among various human body hypofunctions due to senescence leads to a difficulty in behavior due to restriction of movement, and causes an increase in lethality due to a decrease in basal metabolism, or the like. Therefore, sarcopenia has been currently classified as a disease rather than a natural phenomenon due to the senescence.

In order to treat such sarcopenia, the development of various drugs has been attempted, but there is no drug that may be used due to side effects of the drug.

Therefore, up to now, the only alternative for treating the sarcopenia is sufficient protein intake and exercise. However, it is contradictory to suggest exercise requiring the movement as a treatment to patients with the sarcopenia caused by the restriction of the movement due to the senescence, as described above.

Moreover, actually, it is not only very restrictive for the patients with the sarcopenia (the elderly or the like) to exercise, but also movement itself may be impossible for somebody. Therefore, there are many difficulties in suggesting the exercise as an alternative for treating the sarcopenia.

In this regard, conventionally, many studies on whether or not regeneration of muscles may be induced by applying electrical stimulation to muscle cells have been conducted. However, these studies have been conducted only using general muscle cells or cell lines, and there is no study on the muscle regeneration efficiency that may be obtained by applying electrical stimulation to senescent muscle cells.

Accordingly, in a customized electrical stimulation providing system and method according to an embodiment of the present invention, a system and method for providing customized electrical stimulation according to senescence information by distinguishing general muscle cells (cells of which senescence does not occur) and senescent muscle cells from each other in consideration of the fact that a strong exercise of the same strength becomes exercise for the general public, but may cause muscle loss in the elderly in a case where the strong exercise of the same strength is taken for the general public and the elderly are suggested.

Conventionally, Korean Patent No. 10-1977734 (entitled "Electrical Stimulator for Muscular Exercise") discloses an electrical stimulator that induces muscular exercise by applying a microcurrent to the body.

RELATED ART DOCUMENT

Patent Document

Korean Patent No. 10-1977734 (registered on May 5, 2019)

SUMMARY

An embodiment of the present invention is directed to providing a customized electrical stimulation providing system and method capable of providing customized electrical stimulation by deciding a senescence degree of body cells on the basis of an actual age or a biological age in order to most effectively activate a muscle function.

In one general aspect, a customized electrical stimulation providing system includes: an electrical stimulation request input unit 100 receiving electrical stimulation mode selection information; an electrical stimulation control unit 200 setting an electrical stimulation control variable according to the electrical stimulation mode selection information and generating a control signal; and an electrical stimulation providing means 300 receiving the control signal generated by the electrical stimulation control unit and providing electrical stimulation, wherein the electrical stimulation mode selection information includes at least one of a beauty mode (muscle loss mode) and a muscle strengthening mode.

The customized electrical stimulation providing system may further include a user information input unit 400 receiving user information for electrical stimulation control.

The electrical stimulation control unit 200 may calculate an actual age group corresponding to an age of the user on the basis of the input user information and set the electrical stimulation control variable according to the calculated actual age group.

In a case where the electrical stimulation mode selection information is the muscle strengthening mode, the electrical stimulation control unit 200 may set the electrical stimulation control variable on the basis of a range of a first predetermined frequency or less in a case where the actual age group is less than or equal to a preset reference age group.

In a case where the electrical stimulation mode selection information is the muscle strengthening mode, the electrical stimulation control unit 200 may set the electrical stimulation control variable on the basis of a range of a frequency exceeding the first predetermined frequency in a case where the actual age group exceeds the preset reference age group.

In a case where the electrical stimulation mode selection information is the beauty mode (muscle loss mode), the electrical stimulation control unit 200 may set the electrical stimulation control variable on the basis of a range of a second predetermined frequency or more regardless of the actual age group.

The customized electrical stimulation providing system may further include a body composition measuring means 500 linked to the user information input unit 400 to measure body composition information on a user who has input the user information.

The electrical stimulation control unit 200 may calculate a biological age group corresponding to a biological age of the user on the basis of the input user information and the measured body composition information and set the electrical stimulation control variable according to the calculated biological age group.

In a case where the electrical stimulation mode selection information is the muscle strengthening mode, the electrical stimulation control unit 200 may set the electrical stimulation control variable on the basis of a range of a first predetermined frequency or less in a case where the actual age group is less than or equal to a preset reference age group.

In a case where the electrical stimulation mode selection information is the muscle strengthening mode, the electrical stimulation control unit 200 may set the electrical stimulation control variable on the basis of a range of a frequency exceeding a first predetermined frequency in a case where the biological age group exceeds a preset reference age group.

In a case where the electrical stimulation mode selection information is the beauty mode (muscle loss mode), the electrical stimulation control unit 200 may set the electrical stimulation control variable on the basis of a range of a second predetermined frequency or more regardless of the biological age group.

In another general aspect, a customized electrical stimulation providing method includes: an electrical stimulation request step (S100) of receiving electrical stimulation mode selection information by an electrical stimulation request input unit; an electrical stimulation control step (S200) of setting an electrical stimulation control variable according to the electrical stimulation mode selection information received in the electrical stimulation request step (S100) and generating a control signal, by the electrical stimulation control unit; and an electrical stimulation providing step (S300) of receiving the control signal generated in the electrical stimulation control step (S200) and providing electrical stimulation, by an electrical stimulation providing means, wherein the electrical stimulation mode selection information includes at least one of a beauty mode (muscle loss mode) and a muscle strengthening mode.

The electrical stimulation request step (S100) may further include a user information input step (S110) of receiving user information for electrical stimulation control by a user information input unit after receiving the electrical stimulation mode selection information.

In the electrical stimulation control step (S200), an actual age group corresponding to an age of a user may be calculated on the basis of the user information of the user received in the user information input step (S110), and the electrical stimulation control variable according to the calculated actual age group may be set.

In the electrical stimulation control step (S200), in a case where the electrical stimulation mode selection information is the muscle strengthening mode, the electrical stimulation control variable may be set on the basis of a range of a first predetermined frequency or less in a case where the actual age group is less than or equal to a preset reference age group.

In the electrical stimulation control step (S200), in a case where the electrical stimulation mode selection information is the muscle strengthening mode, the electrical stimulation control variable may be set on the basis of a range of a frequency exceeding the first predetermined frequency in a case where the actual age group exceeds the preset reference age group.

In the electrical stimulation control step (S200), in a case where the electrical stimulation mode selection information is the beauty mode (muscle loss mode), the electrical stimulation control variable may be set on the basis of a range of a second predetermined frequency or more regardless of the actual age group.

The electrical stimulation request step (S100) may further include a body composition measuring step (S120) of measuring body composition information on a user who has input the user information by a body composition measuring means after the user information input step (S110) is performed.

In the electrical stimulation control step (S200), a biological age group corresponding to a biological age of the user may be calculated on the basis of the user information received in the user information input step (S110) and the body composition information measured in the body composition measuring step (S120), and the electrical stimulation control variable according to the calculated biological age group may be set.

In the electrical stimulation control step (S200), in a case where the electrical stimulation mode selection information is the muscle strengthening mode, the electrical stimulation control variable may be set on the basis of a range of a first predetermined frequency or less in a case where the biological age group is less than or equal to a preset reference age group.

In the electrical stimulation control step (S200), in a case where the electrical stimulation mode selection information is the muscle strengthening mode, the electrical stimulation control variable may be set on the basis of a range of a frequency exceeding the first predetermined frequency in a case where the biological age group exceeds the preset reference age group.

In the electrical stimulation control step (S200), in a case where the electrical stimulation mode selection information is the beauty mode (muscle loss mode), the electrical stimulation control variable may be set on the basis of a range of a second predetermined frequency or more regardless of the biological age group.

DETAILED DESCRIPTION OF MAIN ELEMENTS

Figure 1:
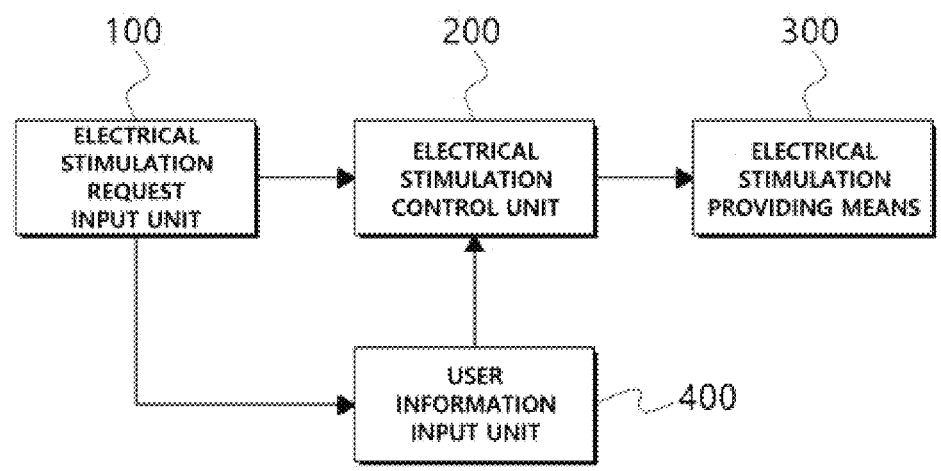
FIG. 1 is an exemplary configuration diagram illustrating a customized electrical stimulation providing system according to a first embodiment of the present invention.

100: electrical stimulation request input unit
200: electrical stimulation control unit
300: electrical stimulation providing means
400: user information input unit
500: body composition measuring means

DETAILED DESCRIPTION OF EMBODIMENTS

Hereinafter, a customized electrical stimulation providing system according to the present invention will be described in detail with reference to the accompanying drawings. Drawings to be provided below are provided by way of example so that the spirit of the present invention may be sufficiently transferred to those skilled in the art. Therefore, the present invention is not limited to drawings to be provided below, but may be implemented in other forms. In addition, like reference numerals denote like components throughout the specification.

In this case, technical terms and scientific terms used in the present specification have the meaning understood by those skilled in the art to which the present invention pertains unless otherwise defined, and a description for known functions and configurations unnecessarily obscuring the gist of the present invention will be omitted in the following description and the accompanying drawings.

In addition, a system refers to a set of components including devices, mechanisms, means, and the like, systematized in order to perform required functions and regularly interacting with one another.

A customized electrical stimulation providing system and method according to an embodiment of the present invention relate to a system and method capable of most efficiently providing muscle recovery of each muscle by distinguishing general muscle cells and senescent muscle cells from each other and generating an electrical stimulation control signal that may induce an increase in a function of each muscle.

In detail, a customized electrical stimulation providing system and method according to an embodiment of the present invention relate to a system and method capable of most efficiently providing muscle recovery of each muscle by obtaining an analysis result of inducing muscle recovery when they are applied to a general muscle but inducing muscle damage when they are applied to a senescent muscle or inducing muscle damage when they are applied to a general muscle but inducing muscle recovery when they are applied to a senescent muscle, according to a provided electrical stimulation control variable through various experiments.

Through this, there is an advantage that it is possible to secure an original technology for the development of a customized electronic drug for muscle recovery or muscle strengthening, and furthermore, artificial muscle loss, for each muscle.

FIG. 1 is an exemplary configuration diagram illustrating a customized electrical stimulation providing system according to a first embodiment of the present invention. The customized electrical stimulation providing system according to a first embodiment of the present invention will be described in detail with reference to FIG. 1.

The customized electrical stimulation providing system according to a first embodiment of the present invention is preferably configured to include an electrical stimulation request input unit 100, an electrical stimulation control unit 200, an electrical stimulation providing means 300, and a user information input unit 400, as illustrated in FIG. 1, and the respective components are preferably connected to each other using a wired or wireless network and are preferably connected to each other in a wired manner, a wireless manner, or a mixed manner thereof according to a condition of a space in which they are provided.

The respective components will be described in detail.

The electrical stimulation request input unit 100 preferably receives electrical stimulation mode selection information, which is a request signal for receiving electrical stimulation, from a user (a person who requests and receives the electrical stimulation).

The electrical stimulation mode selection information is preferably configured to include a beauty mode (muscle loss mode) and a muscle strengthening mode.

Accordingly, the electrical stimulation request input unit 100 includes various means for inputting the electrical stimulation mode selection information described above, for example, a smartphone possessed by the user, a separate input means provided in a space receiving electrical stimulation, and the like, and refers to all kinds of means capable of inputting the electrical stimulation mode selection information, and a kind of the electrical stimulation request input unit 100 is not limited.

In this case, the beauty mode (muscle loss mode) refers to a mode for artificially inducing muscle loss for the purpose of beauty or the like, and the muscle strengthening mode refers to a mode for increasing a muscle mass or thickening and enlarging muscle cells.

The electrical stimulation control unit 200 preferably sets an electrical stimulation control variable according to each mode, that is, sets an electrical stimulation control variable of the beauty mode (muscle loss mode) or sets an electrical stimulation control variable of the muscle strengthening mode, according to the electrical stimulation mode selection information received from the electrical stimulation request input unit 100, and generates a control signal according to the set electrical stimulation control variable.

The electrical stimulation control variable controlled according to each mode through the electrical stimulation control unit 200 is preferably configured to include a voltage, a current, a frequency, a time, and the like.

The electrical stimulation control variable controlled according to each mode in the electrical stimulation control unit 200 will be described in detail later.

The electrical stimulation providing means 300 preferably receives the control signal generated by the electrical stimulation control unit 200 and provides electrical stimulation.

The electrical stimulation providing means 300 refers to a means that may be attached (contacted) to a user's body to stimulate a muscle, such as a known electrical stimulator, electrical therapy stimulator, electrical stimulation device, or the like, and a kind of the electrical stimulation providing means 300 is not limited.

The user information input unit 400 preferably receives user information for electrical stimulation control from the user, and may operate as the same means as the electrical stimulation request input unit 100, but this is only an embodiment.

The user information input unit 400 also includes various means for inputting the user information, for example, a smartphone possessed by the user, a separate input means provided in a space receiving electrical stimulation, and the like, and refers to all kinds of means capable of inputting the variable information, and a kind of the user information input unit 400 is not limited.

In this case, the user information is preferably configured to include a name, a date of birth, an age, a gender, a height, and the like, of the user.

The electrical stimulation control unit 200 preferably calculates an actual age group corresponding to an actual age of the user on the basis of the user information of the user input through the user information input unit 400 and sets the electrical stimulation control variable according to the calculated actual age group.

The electrical stimulation control unit 200 preferably sets the electrical stimulation control variable according to the electrical stimulation mode selection information input by the user through the electrical stimulation request input unit 100.

In detail, the electrical stimulation control unit 200 preferably sets an age group of 10s to 40 s as a general cell group, sets an age group of 50s or older as a senescent cell group, and sets different electrical stimulation control variables according to each mode, but this is only an embodiment of the present invention, and an actual age group and a muscle age group may differently appear due to a difference in a life habit or the like.

In other words, in relation to a criterion for dividing the general cell group and the senescent cell group from each other, SA-B-gal positive cells, which are "senescent cells", generally obtained from persons over the age of 65 were used as a criterion for senescence.

A muscle age is indicated on the basis of several indicators such as an increase in expression of an indicator (SA-B-gal) associated with senescence of muscle cells, a decrease in the number and a size of fiber, a decrease in satellite cells, an increase in intramuscular adipose tissue, a decrease in the number and enzyme of mitochondria, and a decrease in strength and function of the fiber, and it may be approximately decided that the progress of senescence has started on the basis of the fact that a decrease in these indicators appears, but there is no quantitative indicator for an accurate senescence progress degree that may be decided as 'muscle senescence'.

Sarcopenia is clinically diagnosed when an indicator is obtained through (Appendicular Skeletal Muscle Mass (ASM))/Height^2 by a method of measuring an actual muscle mass through magnetic resonance imaging (MRI) or dual energy X-ray absorptiometry (DXA) and the obtained indicator decreases by two times or more the standard deviation as compared with an average value of men and women in their 20s and 40s.

In addition, European working group on sarcopenia in older people (EWGSOP) defines the sarcopenia as a decrease in persistent and systemic skeletal muscle mass and muscle strength, and classifies the sarcopenia into the following three stages.

Stage 1: Decrease in muscle mass
Stage 2: Stage 2: Decrease in muscle mass and decrease in muscle strength or muscle function
Stage 3: Stage 3: Decrease in muscle mass, decrease in muscle strength, and decrease in muscle function As such, it is difficult to clearly identify a correlation between indicators utilized in a clinical diagnosis and indicators appearing at cell units, and a criterion for quantitatively classifying a senescent muscle in the clinical diagnosis has been suggested, but more studies on a reliable diagnostic method are still required. Therefore, distinguishment between the 'general cell group' and the 'senescent cell group' in the present invention is only an example, and the 'general cell group' and the 'senescent cell group' may be differently set by a continuous experiment.

For example, the electrical stimulation control unit 200 preferably sets an electrical stimulation control variable corresponding to the muscle strengthening mode of the general cell group and then generates the control signal when an actual age group of the user who has inputted the muscle strengthening mode is 20s, and sets an electrical stimulation control variable corresponding to the muscle strengthening mode of the senescent cell group and then generates the control signal when an actual age group of the user who has inputted the muscle strengthening mode is 70s, using the information input by the user through the electrical stimulation request input unit 100 and the user information input unit 400.

However, an age group criterion for dividing the general cell group and the senescent cell group is only an embodiment of the present invention, and a criterion may be differently set through various experiments.

That is, the age group criterion for dividing the general cell group and the senescent cell group may be set using statistics of data through experiments, such as various papers and academic conferences or a point in time when senescence occurs may be specified through comparison data on a composition ratio, contractility, sizes of muscle fibers and myonuclei, a size of mitochondria, and the like, of muscle cells that may actually specify the senescence of muscle cells between experimental groups for age groups such as 10s, 20s, 30s, 40s, 50s, 60s, and 60s or older, and the point in time may be set as the age group criterion for dividing the general cell group and the senescent cell group.

The electrical stimulation providing means 300 may provide the electrical stimulation according to each case, in other words, according to the muscle strengthening mode of the senescent cells, the muscle strengthening mode of the general cells, and the beauty mode (muscle loss mode) of the general cells, according to the control signal of the electrical stimulation control unit 200.

In detail, in a case of the electrical stimulation control variable such as a voltage, a current, a frequency, and a time in the muscle strengthening mode of the senescent cells, a muscle strengthening phenomenon was confirmed from a low band (0.1 to 1 Hz) to a high band (up to 500 Hz), and in indicators such as a voltage and a time, stimulation is preferably provided at 0.1 V for 2 hours in cell units.

In addition, in a case of the electrical stimulation control variable such as a voltage, a current, a frequency, and a time in the muscle strengthening mode of the general cells, a muscle strengthening phenomenon was confirmed from a low band (0.1 to 1 Hz) to a middle band (up to 50 Hz), and in indicators such as a voltage and a time, stimulation is preferably provided at 0.1 V for 2 hours in cell units.

Finally, in a case of the electrical stimulation control variable such as a voltage, a current, a frequency, and a time in the beauty mode of the general cells, a muscle loss phenomenon was confirmed in a high band (100 to 5000 Hz), and in indicators such as a voltage and a time, stimulation is preferably provided at 0.1 V for 2 hours in cell unit.

The customized electrical stimulation providing system according to a first embodiment of the present invention relates to a system capable of providing customized electrical stimulation using an actual age group based on an actual age directly input by the user.

However, it is natural that there is a difference in muscle strength even in the same age group depending on a life environment, a daily life habit, or the like.

In consideration of this, a customized electrical stimulation providing system according to a second embodiment of the present invention preferably provides customized electrical stimulation using a biological age group by a biological age of the user. The biological age refers to an age determined by deciding a health condition or senescence information of the body.

Figure 2:
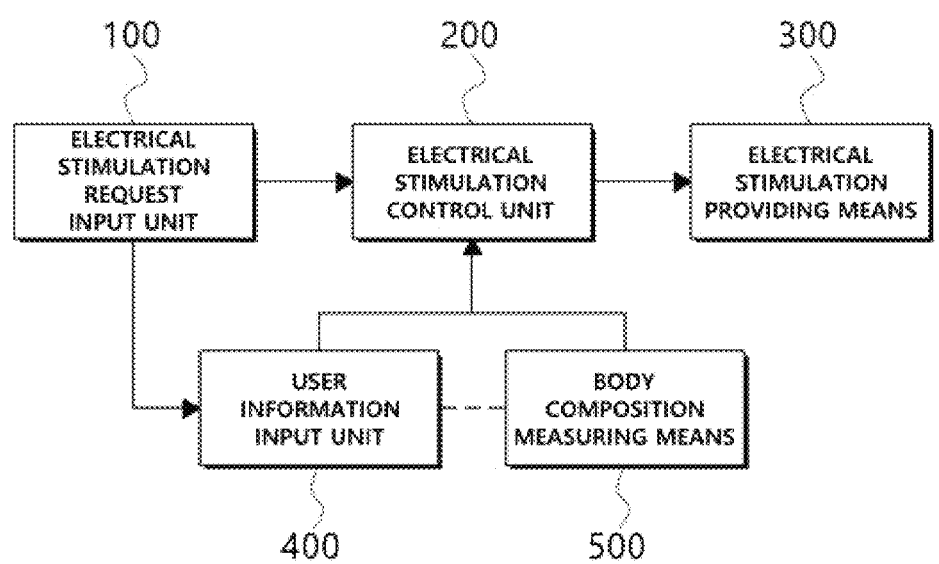
FIG. 2 is an exemplary configuration diagram illustrating a customized electrical stimulation providing system according to a second embodiment of the present invention.
Figure 3:
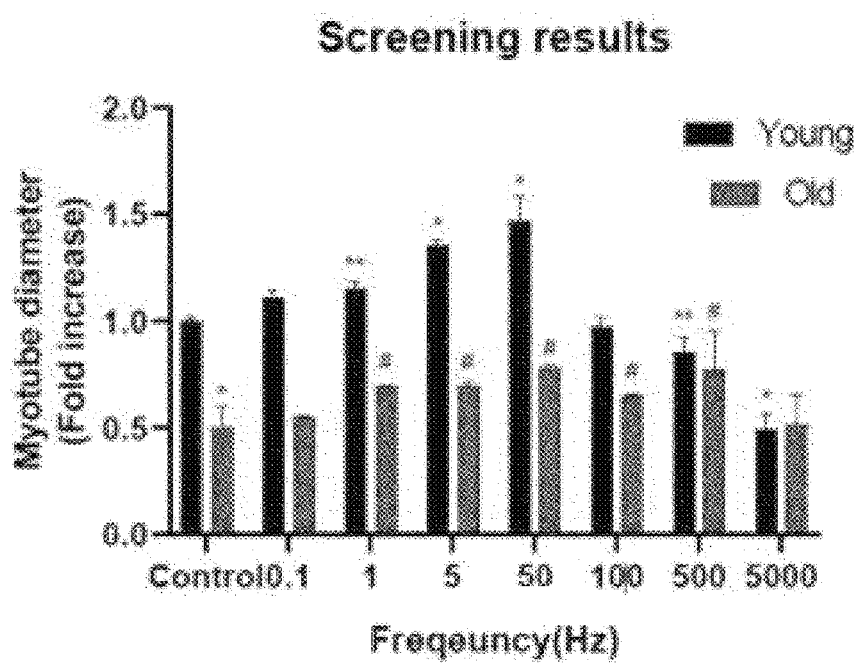
FIGS. 3 to 6 are graphs illustrating a difference in a diameter variation of myotubes between a general cell group and a senescent cell group by a customized electrical stimulation providing system according to an embodiment of the present invention.
Figure 4:
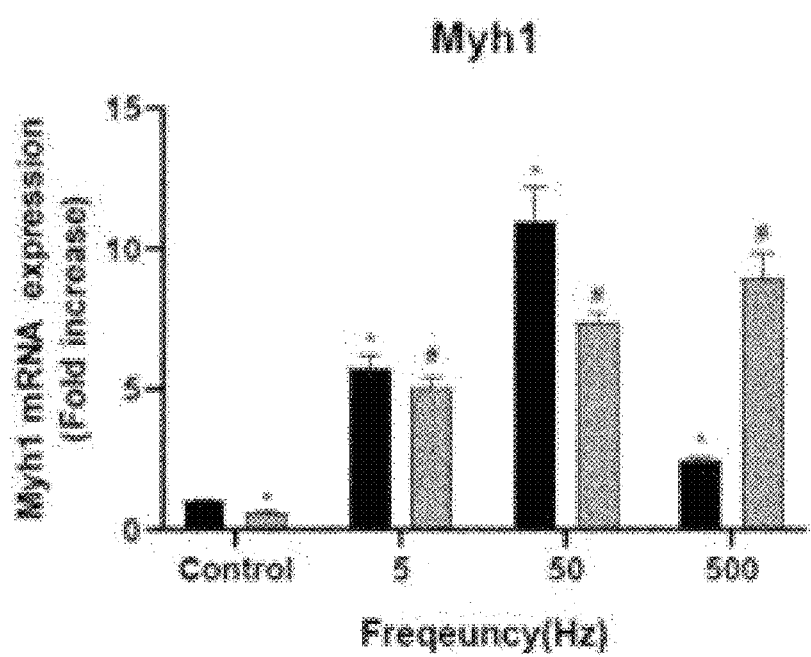
Figure 5:
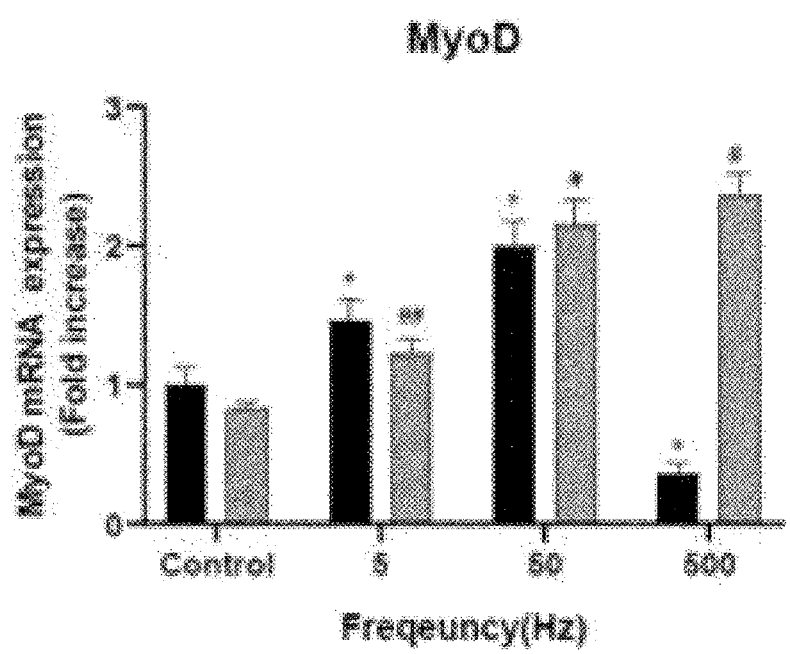
Figure 6:
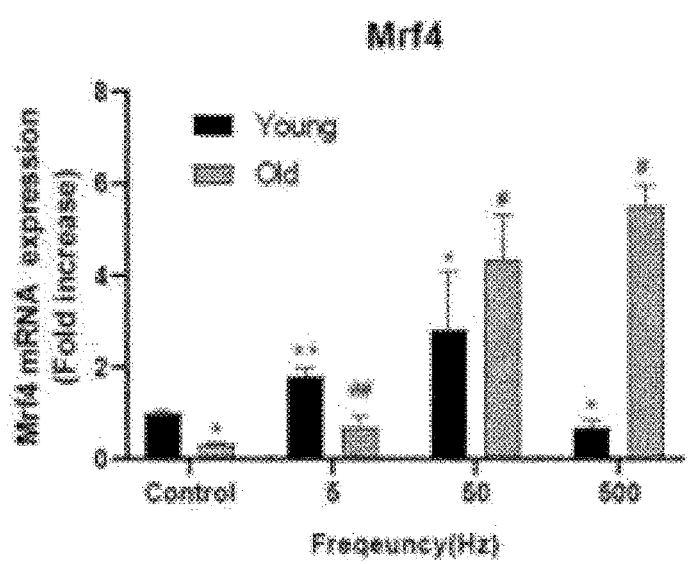

In detail, FIG. 2 is an exemplary configuration diagram illustrating a customized electrical stimulation providing system according to a second embodiment of the present invention. The customized electrical stimulation providing system according to a second embodiment of the present invention will be described in detail with reference to FIG. 2.

The customized electrical stimulation providing system according to a first embodiment of the present invention is preferably configured to include an electrical stimulation request input unit 100, an electrical stimulation control unit 200, an electrical stimulation providing means 300, a user information input unit 400, and a body composition measuring means 500, as illustrated in FIG. 2, and the respective components are preferably connected to each other using a wired or wireless network and are preferably connected to each other in a wired manner, a wireless manner, or a mixed manner thereof according to a condition of a space in which they are provided.

The respective components will be described in detail.

The electrical stimulation request input unit 100 preferably receives electrical stimulation mode selection information, which is a request signal for receiving electrical stimulation, from a user (a person who requests and receives the electrical stimulation).

The electrical stimulation mode selection information is preferably configured to include a beauty mode (muscle loss mode) and a muscle strengthening mode.

Accordingly, the electrical stimulation request input unit 100 includes various means for inputting the electrical stimulation mode selection information described above, for example, a smartphone possessed by the user, a separate input means provided in a space receiving electrical stimulation, and the like, and refers to all kinds of means capable of inputting the electrical stimulation mode selection information, and a kind of the electrical stimulation request input unit 100 is not limited.

In this case, the beauty mode (muscle loss mode) refers to a mode for artificially inducing muscle loss for the purpose of beauty or the like, and the muscle strengthening mode refers to a mode for increasing a muscle mass or thickening and enlarging muscle cells.

The electrical stimulation control unit 200 preferably sets an electrical stimulation control variable according to each mode, that is, sets an electrical stimulation control variable of the beauty mode (muscle loss mode) or sets an electrical stimulation control variable of the muscle strengthening mode, according to the electrical stimulation mode selection information received from the electrical stimulation request input unit 100, and generates a control signal according to the set electrical stimulation control variable.

The electrical stimulation control variable controlled according to each mode through the electrical stimulation control unit 200 is preferably configured to include a voltage, a current, a frequency, a time, and the like.

The electrical stimulation control variable controlled according to each mode in the electrical stimulation control unit 200 will be described in detail later.

The electrical stimulation providing means 300 preferably receives the control signal generated by the electrical stimulation control unit 200 and provides electrical stimulation.

The electrical stimulation providing means 300 refers to a means that may be attached (contacted) to a user's body to stimulate a muscle, such as a known electrical stimulator, electrical therapy stimulator, electrical stimulation device, or the like, and a kind of the electrical stimulation providing means 300 is not limited.

The user information input unit 400 preferably receives user information for electrical stimulation control from the user, and may operate as the same means as the electrical stimulation request input unit 100, but this is only an embodiment.

The user information input unit 400 also includes various means for inputting the user information, for example, a smartphone possessed by the user, a separate input means provided in a space receiving electrical stimulation, and the like, and refers to all kinds of means capable of inputting the variable information, and a kind of the user information input unit 400 is not limited.

In this case, the user information is preferably configured to include a name, a date of birth, an age, a gender, a height, and the like, of the user.

The body composition measuring means 500 is preferably linked to the user information input unit 400 to measure body composition information on the user who has input the user information to the user information input unit 400.

The body composition information is preferably configured to include a body mass index (BMI), a percent body fat (PBF), an organ function, an immunity index, a fitness level, a blood vessel state, a joint state, and the like, and may also be configured to include only a body mass index and a percent body fat that are easily measurable.

The electrical stimulation control unit 200 preferably calculates a biological age group corresponding to a biological age of the user on the basis of the user information of the user input through the user information input unit 400 and the body composition information of the user input through the body composition measuring means 500 and sets the electrical stimulation control variable according to the calculated biological age group.

In detail, the biological age group may be decided by deciding the biological age by correcting the actual age that may be calculated through the user information of the user using the body composition information or by deciding the biological age using only the body composition information.

For example, the biological age group is preferably decided on the basis of blood pressure and electrocardiogram information.

The electrical stimulation control unit 200 preferably sets the electrical stimulation control variable according to the request signal input by the user through the electrical stimulation request input unit 100.

In detail, the electrical stimulation control unit 200 preferably sets an age group of 10s to 40s as a general cell group, sets an age group of 50s or older as a senescent cell group, and sets different electrical stimulation control variables according to each mode.

For example, the electrical stimulation control unit 200 preferably sets an electrical stimulation control variable corresponding to the muscle strengthening mode of the senescent cell group and then generates the control signal when an actual age group of the user who has inputted the muscle strengthening mode is 40s, but a biological age group of the user is 50s, and sets an electrical stimulation control variable corresponding to the muscle strengthening mode of the general cell group and then generates the control signal when an actual age group of the user who has inputted the muscle strengthening mode is 50s, but a biological age group of the user is 30s, using the information related to the user received through the electrical stimulation request input unit 100, the user information input unit 400, and the body composition measuring means 500.

The electrical stimulation control unit 200 preferably sets an electrical stimulation control variable corresponding to the muscle strengthening mode of the senescent cell group and then generates the control signal when an actual age group of the user who has inputted the muscle strengthening mode is 50s, and a biological age group of the user is also 50s.

However, an age group criterion for dividing the general cell group and the senescent cell group is only an embodiment of the present invention, and a criterion may be differently set through various experiments.

That is, the age group criterion for dividing the general cell group and the senescent cell group may be set using statistics of data through experiments, such as various papers and academic conferences or a point in time when senescence occurs may be specified through comparison data on a composition ratio, contractility, sizes of muscle fibers and myonuclei, a size of mitochondria, and the like, of muscle cells that may actually specify the senescence of muscle cells between experimental groups for age groups such as 10s, 20s, 30s, 40s, 50s, 60s, and 60s or older, and the point in time may be set as the age group criterion for dividing the general cell group and the senescent cell group.

The electrical stimulation providing means 300 may provide the electrical stimulation according to each case, in other words, according to the muscle strengthening mode of the senescent cells, the muscle strengthening mode of the general cells, and the beauty mode (muscle loss mode) of the general cells, according to the control signal of the electrical stimulation control unit 200.

In this case, the setting of the electrical stimulation control variable through the electrical stimulation control unit 200 of the customized electrical stimulation providing system according to an embodiment of the present invention may be derived through the experimental graphs illustrated in FIGS. 3 to 9.

Figure 7:
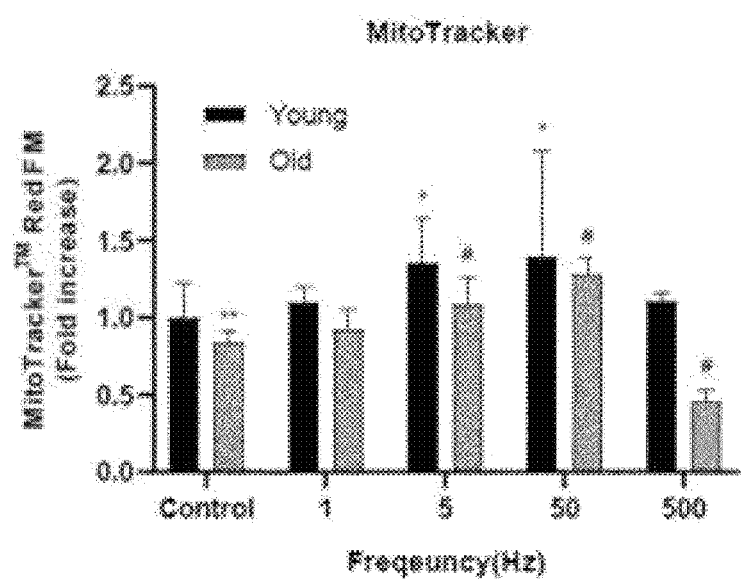
FIGS. 7 and 8 are graphs illustrating variations of Mitotracker Reds and coactivators (PGC-1a genes) for the general cell group and the senescent cell group by the customized electrical stimulation providing system according to an embodiment of the present invention.
Figure 8:
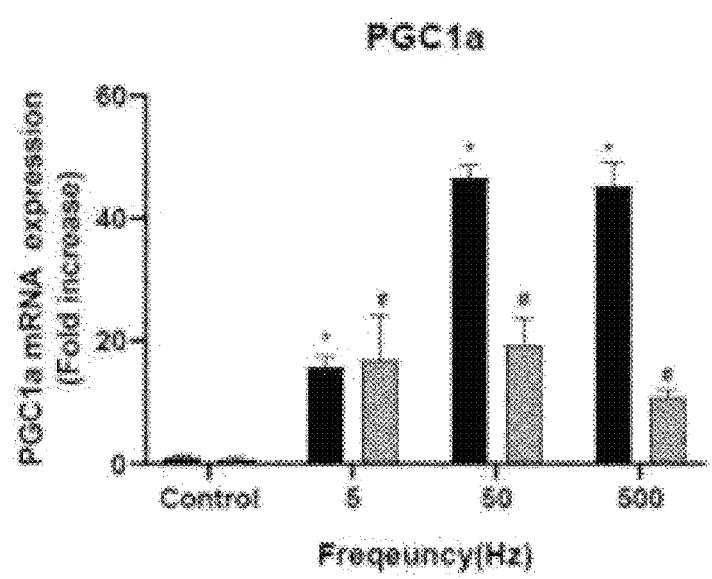
Figure 9:
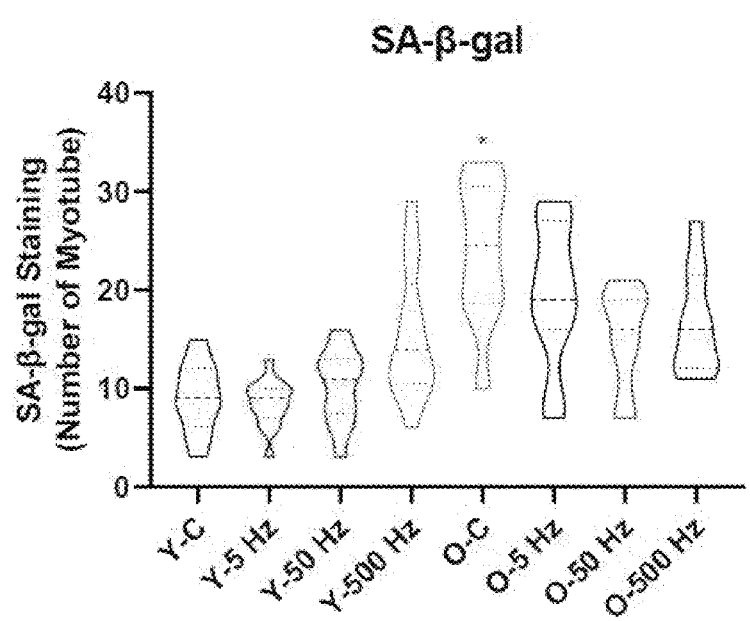
FIG. 9 is graphs illustrating variations of senescence markers (senescence associated beta galactosidase (SA-β-gal)) for the general cell group and the senescent cell group by the customized electrical stimulation providing system according to an embodiment of the present invention.

FIGS. 3 to 6 are graphs illustrating a difference in a diameter variation of myotubes between a general cell group and a senescent cell group, FIGS. 7 and 8 are graphs illustrating variations of Mito-tracker Reds and coactivators (PGC-1a genes) for the general cell group and the senescent cell group, and FIG. 9 is graphs illustrating variations of senescence markers (senescence associated beta galactosidase (SA-β-gal)) for the general cell group and the senescent cell group.

Specifically, it can be seen in FIGS. 3 to 6 that when electrical stimulation having a potential of 0.1 V, a pulse width of 10 ms, and different frequencies is applied to the general cell group and the senescent cell group for 2 hours, diameter variations of myotubes in the general cell group and the senescent cell group differently appear.

That is, in a case of the general cell group, it can be seen that a diameter of the myotube increases at a frequency from 1 to 50 Hz and it can be seen that an increase amount is large particularly at 5 Hz and 50 Hz.

In a case of the senescent cell group, it can be seen that a diameter of the myotube increases at a frequency from 50 to 500 Hz and it can be seen that an increase amount is large particularly at 50 Hz and 500 Hz.

In addition, it can be confirmed that differentiation-related gene expression also increases through qPCR in sections where the diameters of the myotubes increase in each of the general cell group and the senescent cell group.

On the contrary, it can be seen that muscle damage is induced in the general cell group in a case of stimulation having a frequency of 100 Hz or higher, and it can be seen that muscle damage is induced in the senescent cell group at a frequency of 5000 Hz.

It can be seen in FIGS. 7 and 8 that when electrical stimulation having different frequencies is applied to the general cell group and the senescent cell group, variations of Mito-tracker Reds indicating metabolism of the general cell group and the senescent cell group and coactivators, which are genes highly related to the metabolism differently appear.

That is, it can be seen that in both the general cell group and the senescent cell group, effects of the Mito Tracker Reds are high at 5 Hz, 50 Hz, and 500 Hz and expression amounts of the coactivators also increase significantly at 5 Hz, 50 Hz, and 500 Hz, such that it can be seen that there is an effect in increasing not only a muscle mass but also a metabolic ability.

It can be seen in FIG. 9 that when electrical stimulation having different frequencies to applied to the general cell group and the senescent cell group, variations of the senescence markers (senescence associated beta galactosidase (SA-β-gal)) of the general cell group and the senescent cell group differently appear.

That is, it can be seen that when staining of SA-β-gal, which is the senescence marker, is performed, β-gal positive cells significantly increase at 500 Hz in the general cell group and β-gal positive cells decrease at 5 Hz, 50 Hz, and 500 Hz in the senescent cell group.

In a case where such results of the variations of the senescence markers of FIG. 9 are analyzed together with results of the variations of the Mito Tracker Reds and the co-activators of FIGS. 7 and 8, it can be seen that frequencies of 5 and 50 Hz are effective for increasing a function of the general cell group, and it can be seen that at the frequency of 500 Hz, muscle loss is induced, but energy metabolism may be increased, so the frequency of 500 Hz may be utilized as a frequency of the beauty mode (muscle loss mode) for beauty purposes.

In addition, it can be seen that the frequencies of 50 and 500 Hz are effective in order to increase the function of the senescent cell group, such that it can be seen that the frequencies of 50 and 500 Hz may be utilized as frequencies of the muscle strengthening mode.

In consideration of this, the electrical stimulation control unit 200 preferably sets the electrical stimulation control variable on the basis of a range of a first predetermined frequency or less in a case where the decided age group (the actual age group or the biological age group) of the user is less than or equal to a preset reference age group (an age group dividing the general cell group and the senescent cell group), that is, in a case where the age group of the user is the general cell group.

In this case, the first predetermined frequency or less refers to a frequency of 50 Hz or less for increasing the function of the general cell group.

In addition, the electrical stimulation control unit 200 preferably sets the electrical stimulation control variable on the basis of a range of a frequency exceeding the first predetermined frequency in a case where the decided age group (the actual age group or the biological age group) of the user exceeds the preset reference age group (the age group dividing the general cell group and the senescent cell group), that is, in a case where the age group of the user is the senescent cell group.

In this case, the frequency exceeding the first predetermined frequency refers to a frequency of 50 Hz or more to 500 Hz or less for increasing the function of the senescent cell group.

In addition, in a case where the user requests the 'beauty mode (muscle loss mode)', the electrical stimulation control unit 200 preferably sets the electrical stimulation control variable on the basis of a range of a second predetermined frequency or more, regardless of the decided age group (the actual age group or the biological age group) of the user.

In this case, the second predetermined frequency or more refers to a frequency of 500 Hz or more in both the general cell group and the senescent cell group.

Figure 10:
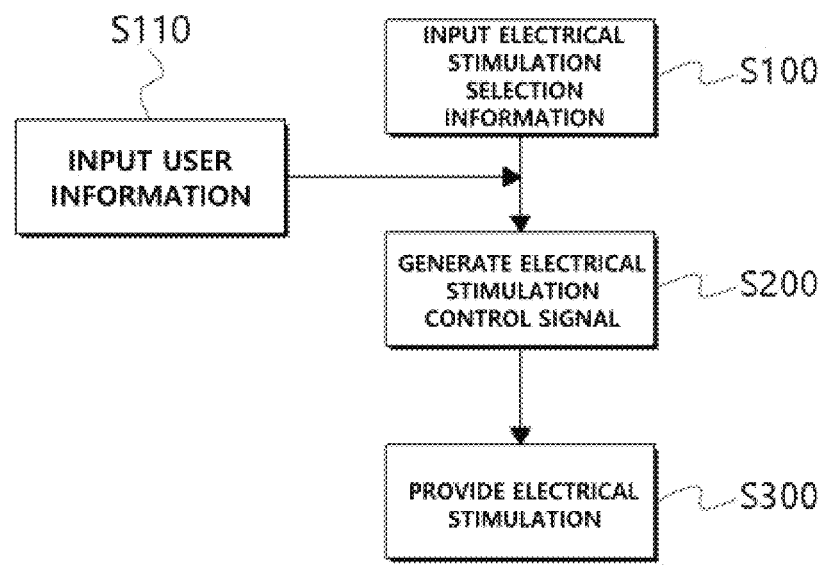
FIG. 10 is an exemplary flowchart illustrating a customized electrical stimulation providing method according to an embodiment of the present invention.

FIG. 10 is an exemplary flowchart illustrating a customized electrical stimulation providing method according to an embodiment of the present invention. The customized electrical stimulation providing method according to an embodiment of the present invention will be described in detail with reference to FIG. 10.

The customized electrical stimulation providing method according to an embodiment of the present invention preferably includes an electrical stimulation request step (S100), an electrical stimulation control step (S200), and an electrical stimulation providing step (S300), as illustrated in FIG. 10.

The respective steps will be described in detail.

In the electrical stimulation request step (S100), it is preferable to receive the electrical stimulation mode selection information from the user (the person who requests and receives the electrical stimulation) by the electrical stimulation request input unit 100.

The electrical stimulation mode selection information received through the electrical stimulation request input unit 100 is preferably configured to include the beauty mode (muscle loss mode) and the muscle strengthening mode.

In this case, the beauty mode (muscle loss mode) refers to a mode for artificially inducing muscle loss for the purpose of beauty or the like, and the muscle strengthening mode refers to a mode for increasing a muscle mass or thickening and enlarging muscle cells.

In the electrical stimulation control step (S200), it is preferable to set an electrical stimulation control variable according to each mode, that is, set an electrical stimulation control variable of the beauty mode (muscle loss mode) or set an electrical stimulation control variable of the muscle strengthening mode, according to the electrical stimulation mode selection information received in the electrical stimulation request step (S100), and generate a control signal according to the set electrical stimulation control variable, by the electrical stimulation control unit 200.

The electrical stimulation control variable controlled according to each mode in the electrical stimulation control step (S200) is preferably configured to include a voltage, a current, a frequency, a time, and the like.

Such an electrical stimulation control variable controlled according to each mode will be described in detail later.

In the electrical stimulation providing step (S300), it is preferable to receive the control signal generated in the electrical stimulation control step (S200) and provide electrical stimulation, by the electrical stimulation providing means 300.

In the electrical stimulation control step (S200), it is preferable to receive user-related information from the user and reflect the user-related information to generate the control signal, rather than to set the electrical stimulation control variable according to each mode using only the electrical stimulation mode selection information received in the electrical stimulation request step (S100) and generate the control signal according to the set electrical stimulation control variable.

In detail, the electrical stimulation request step (S100) is preferably configured to further include a user information input step (S110), as illustrated in FIG. 10.

In the user information input step (S110), it is preferable to receive user information from the user by the user information input unit 400 after receiving the electrical stimulation mode selection information.

In this case, the user information is preferably configured to include a name, a date of birth, an age, a gender, a height, and the like, of the user.

Through this, in the electrical stimulation control step (S200), it is preferable to calculate an actual age group corresponding to an actual age of the user on the basis of the user information of the user received in the user information input step (S110) and set the electrical stimulation control variable according to the calculated actual age group.

In the electrical stimulation control step (S200), it is preferable to set the electrical stimulation control variable according to the electrical stimulation mode selection information input by the user in the electrical stimulation request input step (S100).

In detail, in the electrical stimulation control step (S200), it is preferable to set an age group of 10s to 40s as a general cell group, set an age group of 50s or older as a senescent cell group, and set different electrical stimulation control variables according to each mode.

For example, in the electrical stimulation control step (S200) it is preferable to set an electrical stimulation control variable corresponding to the muscle strengthening mode of the general cell group and then generates the control signal when an actual age group of the user who has inputted the muscle strengthening mode is 20s, and sets an electrical stimulation control variable corresponding to the muscle strengthening mode of the senescent cell group and then generates the control signal when an actual age group of the user who has inputted the muscle strengthening mode is 70s, using the information input by the user in the electrical stimulation request step (S100) and the user information input step (S110).

However, an age group criterion for dividing the general cell group and the senescent cell group is only an embodiment of the present invention, and a criterion may be differently set through various experiments.

That is, the age group criterion for dividing the general cell group and the senescent cell group may be set using statistics of data through experiments, such as various papers and academic conferences or a point in time when senescence occurs may be specified through comparison data on a composition ratio, contractility, sizes of muscle fibers and myonuclei, a size of mitochondria, and the like, of muscle cells that may actually specify the senescence of muscle cells between experimental groups for age groups such as 10s, 20s, 30s, 40s, 50s, 60s, and 60s or older, and the point in time may be set as the age group criterion for dividing the general cell group and the senescent cell group.

In the electrical stimulation providing step (S300), the electrical stimulation according to each case, in other words, according to the muscle strengthening mode of the senescent cells, the muscle strengthening mode of the general cells, and the beauty mode (muscle loss mode) of the general cells may be provided according to the control signal generated in the electrical stimulation control step (S200).

As described above, in a case where the electrical stimulation is provided using the information input in the electrical stimulation request step (S100) and the user information input step (S110) in the electrical stimulation control step (S200), the customized electrical stimulation may be provided using the actual age group directly input by the user.

However, it is natural that there is a difference in muscle strength even in the same age group depending on a life environment, a daily life habit, or the like.

In consideration of this, customized electrical stimulation may also be provided using a biological age group by a biological age of the user. In this case, the biological age refers to an age determined by deciding a health condition or senescence information of the body.

Figure 11:
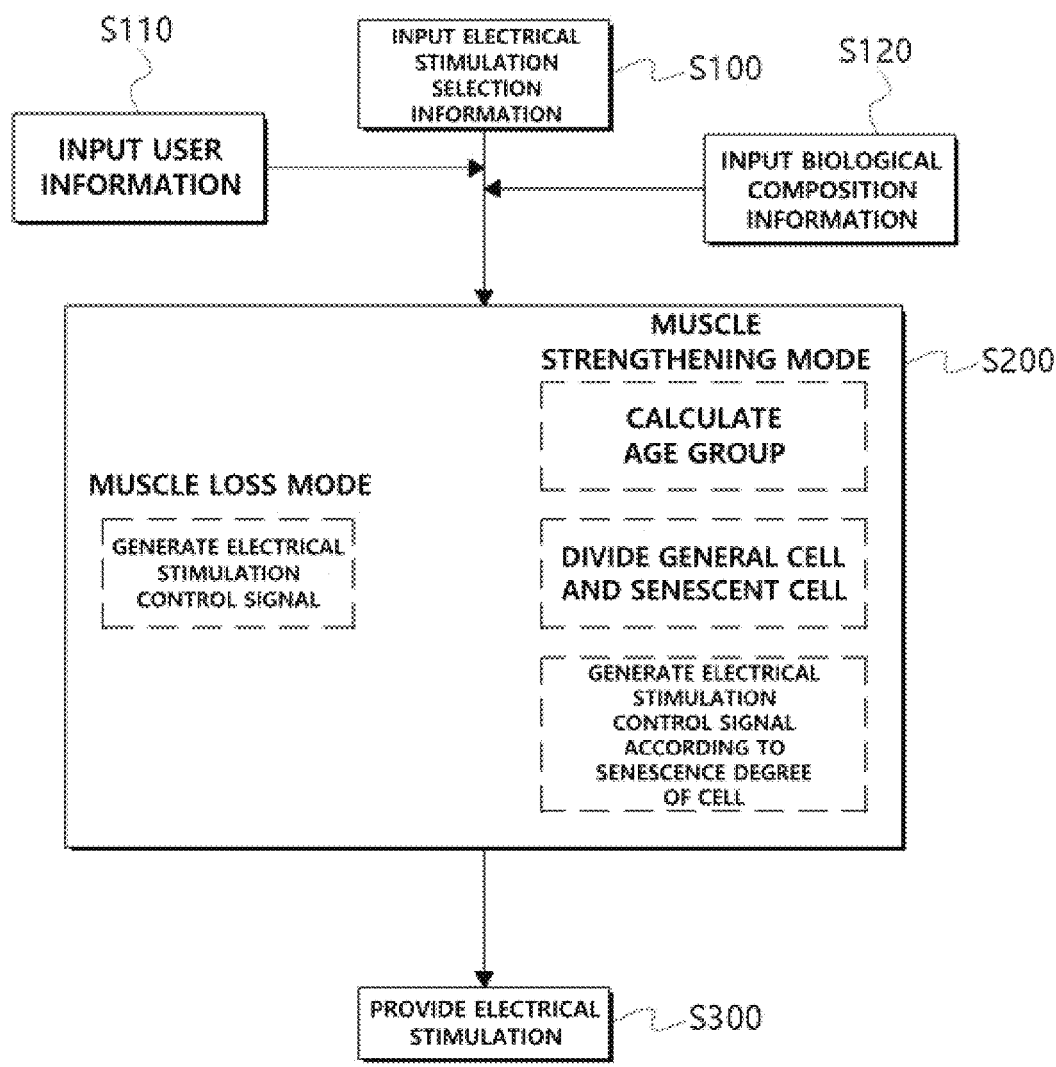
FIG. 11 is an exemplary flowchart illustrating a customized electrical stimulation providing method according to another embodiment of the present invention.

In detail, as illustrated in FIG. 11, in the electrical stimulation request step (S100), it is preferable to further perform a body composition measuring step (S120) of measuring body composition information on the user who has input the variable information after the user information input step (S110) is performed, in other words, after the electrical stimulation mode selection information is received and the user information is received in the user information input step (S110).

In this case, the measured body composition information is preferably configured to include a body mass index (BMI), a percent body fat (PBF), an organ function, an immunity index, a fitness level, a blood vessel state, a joint state, and the like, and may also be configured to include only a body mass index and a percent body fat that are easily measurable.

As described above, in a case where the electrical stimulation mode selection information, the user information, and the body composition information are input in the electrical stimulation request step (S100), in the electrical stimulation control step (S200), it is preferable to calculate a biological age group corresponding to a biological age of the user using the electrical stimulation mode selection information, the user information, and the body composition information and set the electrical stimulation control variable according to the calculated biological age group.

In detail, the biological age group may be decided by deciding the biological age by correcting the actual age, which is the user information of the user, using the body composition information or by deciding the biological age using only the body composition information.

For example, in the electrical stimulation control step (S200), it is preferable to set an electrical stimulation control variable corresponding to the muscle strengthening mode of the senescent cell group and then generate the control signal when an actual age group of the user who has inputted the muscle strengthening mode is 40s, but a biological age group of the user is 50s, and set an electrical stimulation control variable corresponding to the muscle strengthening mode of the general cell group and then generate the control signal when an actual age group of the user who has inputted the muscle strengthening mode is 50s, but a biological age group of the user is 30s, using the information related to the user received in the electrical stimulation request step (S100).

It is preferable to set an electrical stimulation control variable corresponding to the muscle strengthening mode of the senescent cell group and then generate the control signal when an actual age group of the user who has inputted the muscle strengthening mode is 50s, and a biological age group of the user is also 50s.

However, an age group criterion for dividing the general cell group and the senescent cell group is only an embodiment of the present invention, and a criterion may be differently set through various experiments.

That is, the age group criterion for dividing the general cell group and the senescent cell group may be set using statistics of data through experiments, such as various papers and academic conferences or a point in time when senescence occurs may be specified through comparison data on a composition ratio, contractility, sizes of muscle fibers and myonuclei, a size of mitochondria, and the like, of muscle cells that may actually specify the senescence of muscle cells between experimental groups for age groups such as 10s, 20s, 30s, 40s, 50s, 60s, and 60s or older, and the point in time may be set as the age group criterion for dividing the general cell group and the senescent cell group.

In this case, the setting of the electrical stimulation control variable in the customized electrical stimulation providing method according to an embodiment of the present invention may be derived through the experimental graphs illustrated in FIGS. 3 to 9.

FIGS. 3 to 6 are graphs illustrating a difference in a diameter variation of myotubes between a general cell group and a senescent cell group, FIGS. 7 and 8 are graphs illustrating variations of Mito-tracker Reds and coactivators (PGC-1a genes) for the general cell group and the senescent cell group, and FIG. 9 is graphs illustrating variations of senescence markers (senescence associated beta galactosidase (SA-β-gal)) for the general cell group and the senescent cell group.

Specifically, it can be seen in FIGS. 3 to 6 that when electrical stimulation having a potential of 0.1 V, a pulse width of 10 ms, and different frequencies is applied to the general cell group and the senescent cell group for 2 hours, diameter variations of myotubes in the general cell group and the senescent cell group differently appear.

That is, in a case of the general cell group, it can be seen that a diameter of the myotube increases at a frequency from 1 to 50 Hz and it can be seen that an increase amount is large particularly at 5 Hz and 50 Hz.

In a case of the senescent cell group, it can be seen that a diameter of the myotube increases at a frequency from 50 to 500 Hz and it can be seen that an increase amount is large particularly at 50 Hz and 500 Hz.

In addition, it can be confirmed that differentiation-related gene expression also increases through qPCR in sections where the diameters of the myotubes increase in each of the general cell group and the senescent cell group.

On the contrary, it can be seen that muscle damage is induced in the general cell group in a case of stimulation having a frequency of 100 Hz or higher, and it can be seen that muscle damage is induced in the senescent cell group at a frequency of 5000 Hz.

It can be seen in FIGS. 7 and 8 that when electrical stimulation having different frequencies is applied to the general cell group and the senescent cell group, variations of Mito-tracker Reds indicating metabolism of the general cell group and the senescent cell group and coactivators, which are genes highly related to the metabolism differently appear.

That is, it can be seen that in both the general cell group and the senescent cell group, effects of the Mito Tracker Reds are high at 5 Hz, 50 Hz, and 500 Hz and expression amounts of the coactivators also increase significantly at 5

Hz, 50 Hz, and 500 Hz, such that it can be seen that there is an effect in increasing not only a muscle mass but also a metabolic ability.

It can be seen in FIG. 9 that when electrical stimulation having different frequencies to applied to the general cell group and the senescent cell group, variations of the senescence markers (senescence associated beta galactosidase (SA-β-gal)) of the general cell group and the senescent cell group differently appear.

That is, it can be seen that when staining of SA-β-gal, which is the senescence marker, is performed, β-gal positive cells significantly increase at 500 Hz in the general cell group and β-gal positive cells decrease at 5 Hz, 50 Hz, and 500 Hz in the senescent cell group.

In a case where such results of the variations of the senescence markers of FIG. 9 are analyzed together with results of the variations of the Mito Tracker Reds and the co-activators of FIGS. 7 and 8, it can be seen that frequencies of 5 and 50 Hz are effective for increasing a function of the general cell group, and it can be seen that at a frequency of 500 Hz, muscle loss is induced, but energy metabolism may be increased, so the frequency of 500 Hz may be utilized as a frequency of the beauty mode (muscle loss mode) for beauty purposes.

In addition, it can be seen that the frequencies of 50 and 500 Hz are effective in order to increase the function of the senescent cell group, such that it can be seen that the frequencies of 50 and 500 Hz may be utilized as frequencies of the muscle strengthening mode.

In consideration of this, in the electrical stimulation control step (S200), it is preferable to set the electrical stimulation control variable on the basis of a range of a first predetermined frequency or less in a case where the decided age group (the actual age group or the biological age group) of the user is less than or equal to a preset reference age group (an age group dividing the general cell group and the senescent cell group), that is, in a case where the age group of the user is the general cell group.

In this case, the first predetermined frequency or less refers to a frequency of 50 Hz or less for increasing the function of the general cell group.

In addition, it is preferable to set the electrical stimulation control variable on the basis of a range of a frequency exceeding the first predetermined frequency in a case where the decided age group (the actual age group or the biological age group) of the user exceeds the preset reference age group (the age group dividing the general cell group and the senescent cell group), that is, in a case where the age group of the user is the senescent cell group.

In this case, the frequency exceeding the first predetermined frequency refers to a frequency of 50 Hz or more to 500 Hz or less for increasing the function of the senescent cell group.

In addition, in a case where the user requests the 'beauty mode (muscle loss mode)', it is preferable to set the electrical stimulation control variable on the basis of a range of a second predetermined frequency or more, regardless of the decided age group (the actual age group or the biological age group) of the user.

In this case, the second predetermined frequency or more refers to a frequency of 500 Hz or more in both the general cell group and the senescent cell group.

As described above, the customized electrical stimulation providing system and method according to an embodiment of the present invention may double a muscle strengthening effect by controlling various conditions of the electrical stimulation according to a muscle senescence degree of the user according to the muscle strengthening mode and applying the electrical stimulation.

The customized electrical stimulation providing system and method according to an embodiment of the present invention may obtain a result that an exercise effect appears for some users and muscle loss occurs for the other users in a case in which electrical stimulation having the same strength is applied to users according to a muscle senescence degree of the user through various experiments, and double a muscle strengthening effect by controlling various conditions of the electrical stimulation according to the muscle senescence degree of the user.

Through this, optimized electrical stimulation may be provided to a user having difficulty in vigorous physical activity according to senescence, a specific disease, an illness, or a physical condition may, which is effective to treating in preventing sarcopenia.

In addition, there is an advantage that it is possible to secure an original technology for the development of a customized electronic drug for muscle recovery or muscle strengthening, and furthermore, artificial muscle loss, for each muscle (general cell/senescent cell).

The present invention has been described by specific matters such as detailed components, embodiments, and the drawings hereinabove, but they have been provided only for assisting in the entire understanding of the present invention, and the present invention is not limited to embodiments. Various modifications and changes may be made by those skilled in the art to which the present invention pertains from this description.

Therefore, the spirit of the present invention should not be limited to these embodiments, but the claims and all of modifications equal or equivalent to the claims are intended to fall within the scope and spirit of the present invention.

What is claimed is:

1. A customized electrical stimulation providing system comprising:
    an electrical stimulation request input unit configured to receive electrical stimulation mode selection information;
    an electrical stimulation control unit configured to set an electrical stimulation control variable according to the electrical stimulation mode selection information and generate a control signal;
    an electrical stimulation providing unit configured to receive the control signal generated by the electrical stimulation control unit and provide electrical stimulation; and
    a user information input unit configured to receive user information for electrical stimulation control,
    wherein the electrical stimulation mode selection information includes at least one of a beauty mode (muscle loss mode) and a muscle strengthening mode,
wherein the electrical stimulation control unit calculates an actual age group corresponding to an age of the user on the basis of the input user information and sets the electrical stimulation control variable according to the calculated actual age group, and
    wherein in a case where the electrical stimulation mode selection information is the muscle strengthening mode,
    sets the electrical stimulation control variable on the basis of a range of a first predetermined frequency or less in a case where the actual age group is less than or equal to a preset reference age group, and sets the electrical stimulation control variable on the basis of a range of a frequency exceeding the first predetermined frequency in a case where the actual age group exceeds the preset reference age group.

2. A customized electrical stimulation providing system comprising:
an electrical stimulation request input unit configured to receive electrical stimulation mode selection information;
an electrical stimulation control unit configured to set an electrical stimulation control variable according to the electrical stimulation mode selection information and generate a control signal;
an electrical stimulation providing unit configured to receive the control signal generated by the electrical stimulation control unit and provide electrical stimulation; and
a user information input unit configured to receive user information for electrical stimulation control,
wherein the electrical stimulation mode selection information includes at least one of a beauty mode (muscle loss mode) and a muscle strengthening mode,
wherein the electrical stimulation control unit calculates an actual age group corresponding to an age of the user on the basis of the input user information and sets the electrical stimulation control variable according to the calculated actual age group, and
wherein in a case where the electrical stimulation mode selection information is the beauty mode (muscle loss mode), the electrical stimulation control unit sets the electrical stimulation control variable on the basis of a range of a second predetermined frequency or more.

3. A customized electrical stimulation providing system comprising:
an electrical stimulation request input unit configured to receive electrical stimulation mode selection information;
an electrical stimulation control unit configured to set an electrical stimulation control variable according to the electrical stimulation mode selection information and generate a control signal;
an electrical stimulation providing unit configured to receive the control signal generated by the electrical stimulation control unit and provide electrical stimulation; and
a user information input unit configured to receive user information for electrical stimulation control;
a body composition measuring unit linked to the user information input unit configured to measure body composition information on a user who has input the user information,
wherein the electrical stimulation mode selection information includes at least one of a beauty mode (muscle loss mode) and a muscle strengthening mode, and
wherein the electrical stimulation control unit calculates a biological age group corresponding to a biological age of the user on the basis of the input user information and the measured body composition information and sets the electrical stimulation control variable according to the calculated biological age group.

4. The customized electrical stimulation providing system of claim 3, wherein in a case where the electrical stimulation mode selection information is the muscle strengthening mode, the electrical stimulation control unit sets the electrical stimulation control variable on the basis of a range of a first predetermined frequency or less in a case where the biological age group is less than or equal to a preset reference age group.

5. The customized electrical stimulation providing system of claim 3, wherein in a case where the electrical stimulation mode selection information is the muscle strengthening mode, the electrical stimulation control unit sets the electrical stimulation control variable on the basis of a range of a frequency exceeding a first predetermined frequency in a case where the biological age group exceeds a preset reference age group.

6. The customized electrical stimulation providing system of claim 3, wherein in a case where the electrical stimulation mode selection information is the beauty mode (muscle loss mode), the electrical stimulation control unit sets the electrical stimulation control variable on the basis of a range of a second predetermined frequency or more.

7. A customized electrical stimulation providing method comprising:
an electrical stimulation request step of receiving electrical stimulation mode selection information by an electrical stimulation request input unit;
an electrical stimulation control step of setting an electrical stimulation control variable according to the electrical stimulation mode selection information received in the electrical stimulation request step and generating a control signal, by the electrical stimulation control unit; and
an electrical stimulation providing step of receiving the control signal generated in the electrical stimulation control step and providing electrical stimulation, by an electrical stimulation providing unit,
wherein the electrical stimulation mode selection information includes at least one of a beauty mode (muscle loss mode) and a muscle strengthening mode,
wherein the electrical stimulation request step further includes a user information input step of receiving user information for electrical stimulation control by a user information input unit,
wherein in the electrical stimulation control step, an actual age group corresponding to an age of a user is calculated on the basis of the user information of the user received in the user information input step, and the electrical stimulation control variable according to the calculated actual age group is set, and
in a case where the electrical stimulation mode selection information is the muscle strengthening mode,
the electrical stimulation control variable is set on the basis of a range of a first predetermined frequency or less in a case where the actual age group is less than or equal to a preset reference age group, and
the electrical stimulation control variable is set on the basis of a range of a frequency exceeding the first predetermined frequency in a case where the actual age group exceeds the preset reference age group.

8. A customized electrical stimulation providing method comprising:
an electrical stimulation request step of receiving electrical stimulation mode selection information by an electrical stimulation request input unit;
an electrical stimulation control step of setting an electrical stimulation control variable according to the electrical stimulation mode selection information received in the electrical stimulation request step and generating a control signal, by the electrical stimulation control unit; and an electrical stimulation providing step of receiving the control signal generated in the electrical stimulation control step and providing electrical stimulation, by an electrical stimulation providing unit, wherein the electrical stimulation mode selection information includes at least one of a beauty mode (muscle loss mode) and a muscle strengthening mode, wherein the electrical stimulation request step further includes a user information input step of receiving user information for electrical stimulation control by a user information input unit, wherein in the electrical stimulation control step, in a case where the electrical stimulation mode selection information is the beauty mode (muscle loss mode), the electrical stimulation control variable is set on the basis of a range of a second predetermined frequency or more regardless of the actual age group.

9. A customized electrical stimulation providing method comprising:
an electrical stimulation request step of receiving electrical stimulation mode selection information by an electrical stimulation request input unit;
an electrical stimulation control step of setting an electrical stimulation control variable according to the electrical stimulation mode selection information received in the electrical stimulation request step and generating a control signal, by the electrical stimulation control unit;
an electrical stimulation providing step of receiving the control signal generated in the electrical stimulation control step and providing electrical stimulation, by an electrical stimulation providing unit; and
a body composition measuring step of measuring body composition information on a user who has input the user information by a body composition measuring unit,
wherein the electrical stimulation mode selection information includes at least one of a beauty mode (muscle loss mode) and a muscle strengthening mode,
wherein the electrical stimulation request step further comprises a user information input step of receiving user information for electrical stimulation control by a user information input unit, and
a user information input step of receiving user information for electrical stimulation control by a user information input unit, and
wherein in the electrical stimulation control step, a biological age group corresponding to a biological age of the user is calculated on the basis of the user information received in the user information input step and the body composition information measured in the body composition measuring step, and the electrical stimulation control variable according to the calculated biological age group is set.

10. The customized electrical stimulation providing method of claim 9, wherein in the electrical stimulation control step, in a case where the electrical stimulation mode selection information is the muscle strengthening mode, the electrical stimulation control variable is set on the basis of a range of a first predetermined frequency or less in a case where the biological age group is less than or equal to a preset reference age group.

11. The customized electrical stimulation providing method of claim 9, wherein in the electrical stimulation control step, in a case where the electrical stimulation mode selection information is the muscle strengthening mode, the electrical stimulation control variable is set on the basis of a range of a frequency exceeding a first predetermined frequency in a case where the biological age group exceeds a preset reference age group.

12. The customized electrical stimulation providing method of claim 9, wherein in the electrical stimulation control step, in a case where the electrical stimulation mode selection information is the beauty mode (muscle loss mode), the electrical stimulation control variable is set on the basis of a range of a second predetermined frequency or more regardless of the biological age group.

* * * * *